United States Patent
Watanabe et al.

(10) Patent No.: US 7,727,602 B2
(45) Date of Patent: Jun. 1, 2010

(54) RECORDING SHEET WITH INK RECEPTIVE LAYER AND COATING LIQUID FOR FORMING INK RECEPTIVE LAYER

(75) Inventors: Manabu Watanabe, Kitakyushu (JP); Hiroyasu Nishida, Kitakyushu (JP)

(73) Assignee: JGC Catalysts and Chemicals Ltd., Kawasaki-shi (JP)

( * ) Notice: Subject to any disclaimer, the term of this patent is extended or adjusted under 35 U.S.C. 154(b) by 1130 days.

(21) Appl. No.: 10/535,865

(22) PCT Filed: Nov. 20, 2003

(86) PCT No.: PCT/JP03/14813

§ 371 (c)(1), (2), (4) Date: May 20, 2005

(87) PCT Pub. No.: WO2004/045861

PCT Pub. Date: Jun. 3, 2004

(65) Prior Publication Data

US 2006/0046000 A1    Mar. 2, 2006

(30) Foreign Application Priority Data

Nov. 21, 2002 (JP) ............................. 2002-338275

(51) Int. Cl.
- B41M 5/52 (2006.01)
- B32B 15/02 (2006.01)

(52) U.S. Cl. .............. 428/32.36; 428/32.32; 428/32.37; 428/378; 428/389

(58) Field of Classification Search ..... 428/32.1–32.38, 428/378, 389
See application file for complete search history.

(56) References Cited

U.S. PATENT DOCUMENTS

| | | | | |
|---|---|---|---|---|
| 2,712,512 | A * | 7/1955 | Biefeld et al. | 442/256 |
| 3,007,878 | A * | 11/1961 | Alexander et al. | 516/80 |
| 3,541,033 | A * | 11/1970 | Buttrick et al. | 524/556 |
| 4,221,687 | A * | 9/1980 | Minagawa et al. | 524/114 |
| 4,770,934 | A * | 9/1988 | Yamasaki et al. | 428/331 |
| 5,182,175 | A | 1/1993 | Sakaki et al. | |
| 5,246,774 | A * | 9/1993 | Sakaki et al. | 428/323 |
| 5,372,884 | A * | 12/1994 | Abe et al. | 428/32.36 |
| 5,500,668 | A * | 3/1996 | Malhotra et al. | 347/105 |
| 5,707,716 | A * | 1/1998 | Yoshino et al. | 428/212 |
| 6,063,538 | A * | 5/2000 | Hayashi et al. | 430/124.53 |
| 6,365,264 | B2 | 4/2002 | Darsillo et al. | |
| 6,410,199 | B1 * | 6/2002 | Ikeuchi et al. | 430/124.54 |
| 6,726,807 | B1 * | 4/2004 | Mathur | 162/181.6 |
| 6,773,771 | B1 | 8/2004 | Ashida et al. | |
| 7,182,984 | B2 * | 2/2007 | Kohno et al. | 428/32.35 |
| 2004/0066446 | A1 * | 4/2004 | Yamaguchi et al. | 347/105 |
| 2004/0201663 | A1 * | 10/2004 | Bringley et al. | 347/105 |

FOREIGN PATENT DOCUMENTS

| | | |
|---|---|---|
| DE | 100 20 346 A1 | 11/2000 |
| EP | 1 036 666 A1 | 9/2000 |
| JP | 60-219084 A | 11/1985 |
| JP | 60-232990 A | 11/1985 |
| JP | 61-43593 A | 3/1986 |
| JP | 62-149475 A | 7/1987 |
| JP | 3-24906 B2 | 4/1991 |
| JP | 03231887 A * | 10/1991 |
| JP | 4-19037 B2 | 3/1992 |
| JP | 04-115984 A | 4/1992 |
| JP | 06-055829 A | 3/1994 |
| JP | 7-025131 A | 1/1995 |
| JP | 10-226153 A | 8/1998 |
| JP | 2000-37946 A | 2/2000 |
| JP | 2001-146071 A | 5/2001 |
| JP | 2001-301322 A | 10/2001 |
| JP | 2002-086892 A | 3/2002 |
| JP | 2002-234247 A | 8/2002 |

OTHER PUBLICATIONS

Machine translation of detailed description of JP 2000-037946 A. Imported as JP2000_037946detail.pdf.*
Machine translation of detailed description of JP 07-025131 A. Imported JP07_025131detail.pdf.*
STN search for basic magnesium sulfate, performed on Feb. 2, 2009 Imported as STN1.pdf.*
STN search for basic calcium sulfate, performed on Feb. 2, 2009 Imported as STN2.pdf.*
First STN search for calcium silicate, performed on Feb. 2, 2009 Imported as STN5.pdf.*
Second STN search for calcium silicate, performed on Feb. 4, 2009 Imported as STN6.pdf.*
STN search performed by EIC on Feb. 4, 2009. Imported as 10535865EICsearch.pdf.*
Overview of Zono-Hige from http://www.ubematerial.com/applications/mp08_zonohigi.pdf. Acquired on Feb. 4, 2009. Imported as zonoihige.pdf.*

* cited by examiner

*Primary Examiner*—Mark Ruthkosky
*Assistant Examiner*—Gerard T Higgins
(74) *Attorney, Agent, or Firm*—The Webb Law Firm

(57) ABSTRACT

A recording sheet with an ink-receptive layer which can be used not only for dye type inks but also for pigment type inks is provided. Also provided is a coating liquid for forming an ink-receptive layer. The recording sheet with an ink-receptive layer includes a substrate sheet and an ink-receptive layer formed thereon, wherein the ink-receptive layer includes (i) fibrous crystalline particles on surfaces of which a cationic hydrated metal compound is supported and (ii) a binder. The fibrous crystalline particles have an average fiber diameter (D) of 0.1 to 2 μm, an average fiber length (L) of 1 to 200 μm and a ratio (aspect ratio) of an average fiber length (L) to an average fiber diameter (D) of 5 to 500.

12 Claims, No Drawings

RECORDING SHEET WITH INK RECEPTIVE LAYER AND COATING LIQUID FOR FORMING INK RECEPTIVE LAYER

TECHNICAL FIELD

The present invention relates to a recording sheet with an ink-receptive layer. More particularly, the invention relates to a recording sheet with an ink-receptive layer on which printing can be clearly made with uniform density, which is capable of firmly fixing dye or the like and which is capable of providing a print having excellent water resistance, weathering resistance and fading resistance and having satisfactory strength.

The present invention also relates to a coating liquid for forming the above-mentioned ink-receptive layer.

BACKGROUND ART

Printing by an ink jet method has rapidly spread and used for various purposes because printing of the same image quality as in the conventional multi-color printing or color photographic system is feasible, speeding up or multi-coloring is easily made, and the cost is lower than the conventional printing methods in case of a small number of sheets to be printed.

In the printing by the ink jet method, a recording sheet having on a substrate sheet an ink-receptive layer formed by coating the substrate sheet with a water-soluble polymer such as polyvinyl alcohol is employed, and on the sheet, printing is carried out by the use of a water base ink. The resulting print, however, has insufficient water resistance, and there is a problem of lowering of image quality in the case where the print is placed in environment of high moisture or is wetted by water. Further, there is another problem that an image of high sharpness and high precision cannot be obtained because the recording sheet used has insufficient ink absorption characteristics.

To solve such problems, a recording sheet wherein an ink-receptive layer containing fine particles of silica, alumina or the like is formed on a substrate sheet is proposed.

For example, in Japanese Patent Laid-Open Publication No. 149475/1987, a recording sheet wherein an ink-receptive layer containing spherical particles of silica or the like having an average particle diameter of 1 to 50 µm is formed is described. In Japanese Patent Publication No. 24906/1991, a recording medium having an ink-receptive layer containing cationic hydrated aluminum oxide is described. In Japanese Patent Publication No. 19037/1992, a recording medium having a receptive layer containing cationic colloidal silica is described. In Japanese Patent Laid-Open Publication No. 115984/1992, a recording sheet wherein a layer of pseudo-boehmite alumina is formed on a substrate and a layer of porous silica is further provided thereon is described. In Japanese Patent Laid-Open Publication No. 55829/1994, a recording sheet having on a substrate a layer of porous silica particles having an average particle diameter of 2 to 50 µm, an average pore diameter of 8 to 50 nm and a pore volume of 0.8 to 2.5 cc/g and further having thereon a pseudo-boehmite porous layer obtained by drying an alumina sol is described.

Most of these recording sheets are intended for printing using dye type inks, but because the dye type inks have poor weathering resistance, the resulting prints have disadvantages such as discoloration or decoloring caused by exposure to ultraviolet light, oxygen, ozone or the like, and such disadvantages are markedly observed especially when the prints are used outdoors.

Therefore, pigment type inks having excellent weathering resistance came to be used even in the ink jet printing method.

Pigment particles, however, are particles usually having diameters of 10 to 500 nm, and the conventional ink-receptive layer does not have pores capable of effectively absorbing such large particles, so that there resides problems such that the pigment particles remain on the ink-receptive layer surface without being absorbed by the ink-receptive layer, the ink-receptive layer exhibits insufficient water resistance, and the pigment particles are removed by rubbing to cause crocking.

The present invention is intended to solve such problems associated with the prior art as described above, and it is an object of the invention to provide a recording sheet with an ink-receptive layer which can be used not only for dye type inks but also for pigment type inks, has excellent printing properties such that a print free from ink blotting is obtainable and clear printing with uniform density is feasible, is excellent in water resistance, weathering resistance and fading resistance and has sufficiently high strength, and a coating liquid for forming an ink-receptive layer.

In particular, it is an object of the invention to provide a recording sheet with an ink-receptive layer which is desirable for high-speed printing by an ink jet method and is favorably used also as a recording sheet, such as white color PET for large size color printer or art paper, or a recording sheet having no absorption characteristics and needing transparency, and a coating liquid for forming an ink-receptive layer.

SUMMARY OF THE INVENTION

The recording sheet with an ink-receptive layer according to the present invention is a recording sheet comprising a substrate sheet and an ink-receptive layer formed thereon, wherein the ink-receptive layer comprises:

(i) fibrous crystalline particles on surfaces of which a cationic hydrated metal compound is supported, and (ii) a binder.

The fibrous crystalline particles are preferably particles of at least one substance selected from the group consisting of basic magnesium sulfate ($MgSO_4 \cdot 5Mg(OH)_2 \cdot nH_2O$), basic calcium sulfate ($CaSO_4 \cdot 5Ca(OH)_2 \cdot nH_2O$), basic barium sulfate ($BaSO_4 \cdot 5Ba(OH)_2 \cdot nH_2O$), basic strontium sulfate ($SrSO_4 \cdot 5Sr(OH)_2 \cdot nH_2O$) and calcium silicate ($Ca_2SiO_4 \cdot nH_2O$).

The fibrous crystalline particles preferably have an average fiber diameter (D) of 0.1 to 2 µm, an average fiber length (L) of 1 to 200 µm and a ratio (aspect ratio) of an average fiber length (L) to an average fiber diameter (D) of 5 to 500.

The cationic hydrated metal compound is preferably a compound represented by the following formula (1) or a compound obtained from a metal salt represented by the following formula (2):

$$[M_2(OH)_nX_{(2a-n)/b}]_m \quad (1)$$

$$[MX_{a/b}]_m \quad (2)$$

wherein M is a trivalent or higher metallic cation, X is an anion, a is a valence of the metallic cation, b is a valence of the anion, and n and m are numbers satisfying the conditions of $1 < n < 5$, $n < 2a$ and $1 \leq m$.

In the cationic hydrated metal compound, M is preferably $Al^{3+}$.

The recording sheet with an ink-receptive layer preferably further comprises inorganic fine particles.

The inorganic fine particles are preferably one or more substances selected from an alumina sol, an alumina gel, a silica sol, a silica gel, a silica-alumina sol, a silica-alumina gel, a zirconia sol, a zirconia gel and a clay mineral.

The inorganic fine particles are preferably an alumina sol and/or an alumina gel each of which is pseudo-boehmite alumina.

The ink-receptive layer preferably has pores having pore diameters of 30 to 2000 nm, and a pore volume of the pores having pore diameters of 30 to 2000 nm is preferably in the range of 0.15 to 2.0 ml/g.

The coating liquid for forming an ink-receptive layer according to the present invention comprises (i) fibrous crystalline particles on surfaces of which a cationic hydrated metal compound is supported and (ii) a binder, said fibrous crystalline particles (i) and said binder (ii) being dispersed in a dispersion medium consisting of water and/or an organic solvent.

DETAILED DESCRIPTION OF THE INVENTION

Recording Sheet with Ink-Receptive Layer

The recording sheet with an ink-receptive layer according to the invention comprises a substrate sheet and an ink-receptive layer formed on the substrate sheet.

Substrate Sheet

The substrate sheet for use in the invention is not specifically restricted, but usually used are film sheets made of resins such as PET and polyvinyl chloride, various papers, steel plates, cloths and the like.

Ink-Receptive Layer

The ink-receptive layer formed on the substrate sheet comprises (i) fibrous crystalline particles on surfaces of which a cationic hydrated metal compound is supported (referred to as "cationic hydrated metal compound-supported fibrous crystalline particles" hereinafter) and (ii) a binder.

(i) Cationic hydrated metal compound-supported fibrous crystalline particles

In the present invention, fibrous crystalline particles on surfaces of which a cationic hydrated metal compound is supported are employed.

The fibrous crystalline particles for use in the invention have a fiber diameter (D) of preferably about 0.1 to 2 µm, more preferably 0.5 to 1 µm, and a fiber length (L) of preferably about 1 to 200 µm, more preferably 3 to 100 µm. A ratio (aspect ratio) of a fiber length (L) to a fiber diameter (D) is in the range of preferably 5 to 500, more preferably 10 to 200.

When such fibrous crystalline particles, particularly fibrous crystalline particles having a high aspect ratio, are contained, they are entangled with one another without being densely filled, and pores are easily formed, whereby a porous ink-receptive layer having a pore volume capable of receiving both of a dye type ink and a pigment type ink can be formed. Further, by virtue of such entanglement of the fibrous crystalline particles, strength of the ink-receptive layer itself can be enhanced.

When such fibrous crystalline particles are contained, an ink-receptive layer having a pore volume capable of receiving both of a dye type ink and a pigment type ink can be formed, and besides, strength of the ink-receptive layer itself can be enhanced. By the use of such fibrous crystalline particles, further, the ink-receptive layer has high transparency, and a clear print can be obtained.

If the fiber diameter (D) of the fibrous crystalline particles is less than 0.1 µm, the pore volume is increased but the strength of the ink-receptive layer becomes insufficient, though it depends upon the length of the fibrous crystalline particles. If the fiber diameter (D) of the fibrous crystalline particles exceeds 2 µm, transparency of the ink-receptive layer is lowered, and the resulting print has insufficient clearness.

If the fiber length (L) of the fibrous crystalline particles is less than 1 µm, the pore volume becomes insufficient, and the ink absorption quantity or the ink absorption rate tends to be decreased to lower printing performance, though it depends upon the fiber diameter of the fibrous crystalline particles.

If the fiber length (L) of the fibrous crystalline particles exceeds 200 µm, the coating liquid obtained has a high viscosity, and it becomes difficult to control a film thickness.

If the aspect ratio is less than 5, an effect given by the use of the fibrous crystalline particles is not sufficient, that is, the pore volume becomes insufficient, and the ink absorption quantity or the ink absorption rate tends to be decreased to lower printing performance.

If the aspect ratio exceeds 500, the coating liquid obtained has a high viscosity, and it becomes difficult to control a film thickness.

Such a size of the fibrous particles is determined in the following manner. A scanning electron microphotograph (SEM photograph) is taken, then fiber diameters and fiber lengths of 20 particles of the photograph are measured, and from average values of the fiber diameters and the fiber lengths, the size is calculated.

The fibrous crystalline particles are not specifically restricted provided that they have the aforesaid shape and size, and for example, particles of a basic alkaline earth metal sulfate compound or an alkaline earth metal silicate compound are employable. More specifically, particles of basic magnesium sulfate ($MgSO_4.5Mg(OH)_2.nH_2O$), basic calcium sulfate ($CaSO_4.5Ca(OH)_2.nH_2O$), basic barium sulfate ($BaSO_4.5Ba(OH)_2.nH_2O$), basic strontium sulfate ($SrSO_4.5Sr(OH)_2.nH_2O$) and calcium silicate ($Ca_2SiO_4.nH_2O$) are employable. Of these, fibrous basic magnesium sulfate is desirably used because it is inexpensive and an ink-receptive layer having large pore diameters, a large pore volume and high strength is obtained. In particular, an ink-receptive layer having an average pore diameter of not less than 30 nm tends to be obtained.

Such a basic alkaline earth metal sulfate compound can be obtained by, for example, subjecting a sulfate of an alkaline earth metal and an alkaline earth metal hydroxide to hydrothermal reaction in an autoclave at a temperature of 100 to 200° C. The size of the fibrous crystalline particles of the resulting basic alkaline earth metal sulfate compound can be controlled by the hydrothermal reaction conditions.

In the present invention, fibrous crystalline particles on surfaces of which a cationic hydrated metal compound is supported are employed. The cationic hydrated metal compound-supported fibrous crystalline particles can be obtained specifically by adding a cationic hydrated metal compound to a dispersion of the fibrous crystalline particles and thereby allowing the surfaces of the particles to support the compound.

As the cationic hydrated metal compound, a compound represented by the following formula (1) is preferably employed.

$$[M_2(OH)_n X_{(2a-n)/b}]_m \qquad (1)$$

wherein M is a trivalent or higher metallic cation, X is an anion, a is a valence of the metallic cation, b is a valence of the anion, and n and m are numbers satisfying the conditions of 1<n<5, n<2a and 1≦m.

The metallic cation is preferably a trivalent or tetravalent metallic cation, and is more preferably a metallic cation of $Al^{3+}$, $Zr^{4+}$, $Ti^{4+}$, $Ga^{4+}$ or the like. The anion is, for example, a halogen ion, a sulfuric acid ion, a nitric acid ion or an organic anion.

The cationic hydrated metal compound can be prepared by a conventional process. For example, the compound can be obtained by a process comprising dissolving aluminum hydroxide in hydrochloric acid under pressure or in the presence of a dissolving assistant to prepare aluminum chloride and aging it in the presence of a polymerization promoter such as sulfuric acid.

A dispersion obtained by dispersing the fibrous crystalline particles in a solvent such as water, methanol, ethanol, isopropyl alcohol or a mixed solvent thereof is mixed with a solution of the cationic hydrated metal compound to perform reaction. In the reaction, an alkali is added to the dispersion to adjust pH of the dispersion, when needed. Although pH of the dispersion varies depending upon the type of the crystalline alumina particles used, it has only to be in the range of about 2 to 9. The pH is more preferably in the range of 3 to 6.

It is possible to prepare the cationic hydrated metal compound from a metal salt represented by the following formula (2).

That is to say, instead of the compound represented by the formula (1) or together with the compound represented by the formula (1), an aqueous solution of a metal salt represented by the following formula (2) is added to a dispersion of the fibrous crystalline particles, then an alkali is added, and pH of the dispersion is adjusted in the above range, whereby fibrous crystalline particles on surfaces of which a cationic hydrated metal compound is supported can be obtained.

$$[MX_{a/b}]_m \quad (2)$$

wherein M, X, a and b have the same meanings as in the aforesaid formula (1).

In the formulas (1) and (2), M is preferably $Al^{3+}$. By the use of such a cationic hydrated metal compound or such a metal salt as mentioned above, the surfaces of the fibrous crystalline particles conspicuously become cationic, and the resulting ink-receptive layer has a high streaming potential (surface charge quantity). On this account, dye or pigment can be firmly fixed, and hence, the ink-receptive layer exhibits excellent water resistance.

The amount of the cationic hydrated metal compound supported (amount supported=amount added; in case of a metal salt represented by the formula (2), amount added; in case of both of (1) and (2), total amount) is in the range of preferably 0.01 to 5 mol, more preferably 0.1 to 2 mol, in terms of a metal oxide, based on 1 mol of the fibrous crystalline particles, such as particles of a basic alkaline earth metal sulfate compound.

If the amount of the compound supported is less than 0.01 mol, the resulting ink-receptive layer has a low streaming potential. Therefore, dye or pigment cannot be firmly fixed, and the ink-receptive layer exhibits insufficient water resistance.

If the amount of the cationic hydrated metal compound based on 1 mol of the fibrous crystalline particles exceeds 5 mol, dispersion stability of the resulting cationic hydrated metal compound-supported fibrous crystalline particles tends to be lowered, and when printing is carried out, dye tends to be adsorbed only on the upper part of the ink-receptive layer to lower image quality.

When the cationic hydrated metal compound is added to a dispersion of the cationic fibrous crystalline particles to treat the particles, the concentration of the fibrous crystalline particles is not specifically restricted provided that cationic hydrated metal compound-supported fibrous crystalline particles having a high streaming potential can be obtained, and the concentration is usually in the range of 1 to 30% by weight. The temperature is in the range of 5 to 60° C. In this treatment, the dispersion has pH of 2 to 7.

The cationic hydrated metal compound-supported fibrous crystalline particles obtained as above are in the same fibrous state as that of the basic alkaline earth metal sulfate compound particles.

The cationic hydrated metal compound-supported fibrous crystalline particles have a streaming potential of preferably 1 to 200 µeq/g, more preferably 2 to 100 µeq/g.

If the streaming potential of (i) the fibrous crystalline particles on surfaces of which the cationic hydrated metal compound is supported is less than 1 µeq/g, dye cannot be firmly fixed and the amount of the dye fixed is small, so that water resistance sometimes becomes insufficient or the resulting print sometimes lacks clearness.

If the streaming potential of the cationic hydrated metal compound-supported fibrous crystalline particles exceeds 200 µeq/g, dye is fixed locally to the upper part of the receptive layer and cannot be fixed to the lower part of the receptive layer, or the pores in the upper part are sometimes choked. On this account, inks are not absorbed or blotting occurs occasionally during multiple printing using different color inks.

The streaming potential of the cationic hydrated metal compound-supported fibrous crystalline particles can be determined in the following manner by the use of a streaming potential measuring device (manufactured by MUTEC K.K., PCD 03PH).

A water dispersion of cationic hydrated metal compound-supported fibrous crystalline particles (solids concentration: 1% by weight) is prepared, then to the dispersion is dropwise added an anionic polyelectrolyte (sodium polyethene sulfonate, Pes-Na) until the potential becomes zero, and a charge quantity is calculated from the following formula.

$$q = V \times c/wt$$

V: titer of electrolyte (L)
C: titrant charge concentration (eq/L)
wt: solids weight (g) of cationic hydrated metal compound-supported fibrous crystalline particles
q: charge quantity (eq/g)

When such cationic hydrated metal compound-supported fibrous crystalline particles are used, an ink-receptive layer wherein a pore volume of pores having pore diameters of 30 to 2000 nm is in the range of 0.2 to 2.0 ml/g, preferably 0.2 to 1.0 ml/g, can be obtained. Therefore, as the printing inks, pigment inks can be favorably used in addition to dye inks. Further, because of high ink absorption rate, the ink-receptive layer is free from ink blotting and exhibits excellent printing properties. Moreover, because the particle surface has a high streaming potential, an ink-receptive layer to which dye can be firmly fixed and which is excellent in water resistance, weathering resistance and fading resistance can be obtained.

In the present invention, the cationic hydrated metal compound-supported fibrous crystalline particles may be used after their surfaces are made hydrophobic, when needed. When the cationic hydrated metal compound-supported fibrous crystalline particles are used after their surfaces are made hydrophobic, adsorption or permeation of water into the ink-receptive layer hardly occurs, and water resistance of the ink-receptive layer is enhanced.

Although a method to make the cationic hydrated metal compound-supported fibrous crystalline particles hydrophobic is not specifically restricted, a conventional method such as a method of treating the cationic hydrated metal compound-supported fibrous crystalline particles with a coupling agent, such as monomethylsilane, monomethyltrimethoxysilane, monomethyltriethoxysilane, dimethyldimethoxysilane, dimethylvinylmethoxysilane, phenyltriethoxysilane, diphenyldimethoxysilane, vinyltrichlorosilane or γ-glycidoxypropyltrimethoxysilane, is available.

Binder

Examples of the binders for use in the invention include polyvinyl alcohol, modified polyvinyl alcohol, polyvinyl pyrrolidone, and organic compounds such as hydrophilic polymers. They may be used after modified.

These binders may be used singly or in combination.

The binder is used in an amount of 5 to 60% by weight, preferably 10 to 40% by weight, based on the cationic hydrated metal compound-supported fibrous crystalline particles, though the amount varies depending upon the type of the binder used.

If the amount of the binder is less than 5% by weight, adhesion strength of the ink-receptive layer to the substrate sheet is insufficient and the ink-receptive layer is liable to peel off, or the ink-receptive layer has insufficient strength. If the amount of the binder exceeds 60% by weight, the amount of ink received is sometimes decreased, or the water resistance is sometimes lowered.

The ink-receptive layer may further contain components which are usually added to an ink-receptive layer, for example, antioxidants, organic polymers, such as celluloses, bio-fibers, inorganic polymers and inorganic fine particles, in addition to the above-mentioned components.

In particular, the ink-receptive layer preferably further contains inorganic fine particles.

The inorganic fine particles are preferably one or more substances selected from an alumina sol, an alumina gel, a silica sol, a silica gel, a silica-alumina sol, a silica-alumina gel, a zirconia sol, a zirconia gel and a clay mineral. The inorganic fine particles are particularly preferably an alumina sol and/or an alumina gel each of which is pseudo-boehmite alumina.

Process for Forming Ink-Receptive Layer

The process for forming an ink-receptive layer on a substrate sheet is not specifically restricted provided that an ink-receptive layer comprising (i) fibrous crystalline particles on surfaces of which a cationic hydrated metal compound is supported and (ii) a binder is formed, and any of publicly known processes is adoptable. According to the type of the substrate, a preferred process is adopted.

More specifically, the ink-receptive layer can be formed by coating a substrate sheet with the later-described coating liquid for forming an ink-receptive layer by a spray method, a roll coater method, a blade coater method, a curtain coater method or the like and then drying the coated layer.

The substrate sheet may be subjected to primer treatment in advance.

The ink-receptive layer formed as above has pores having pore diameters of usually 30 to 2000 nm, and a pore volume of the pores having pore diameters of 30 to 2000 nm is in the range of 0.15 to 2.0 ml/g, preferably 0.2 to 2.0 ml/g, more preferably 0.2 to 1.0 ml/g.

If the pore volume of the pores having pore diameters of 30 to 2000 nm is less than the lower limit of the above range, pigment type ink cannot be absorbed sufficiently. Therefore, the pigment particles remain on the surface of the ink-receptive layer, and these pigment particles sometimes separate off by rubbing to cause crocking of the resulting print. If the pore volume is more than the upper limit of the above range, fixability of the pigment particles is lowered or most of the pigment particles gather in the lower part of the ink-receptive layer (in the vicinity of the substrate surface) after printing, and hence, the image sometimes lacks sharpness.

The thickness of the ink-receptive layer formed on the substrate sheet can be arbitrarily determined according to the thickness of the sheet, purpose of the print, type of the printing ink, etc., but it is desired to be in the range of usually 5 to 100 μm. If the thickness of the ink-receptive layer is less than 5 μm, capacity for ink absorption becomes insufficient to cause ink blotting, or color is sometimes lowered when the amount of ink used is decreased. On the other hand, it is difficult to obtain an ink-receptive layer having a thickness of more than 100 μm by one coating operation, and coating operations of plural times are disadvantages from the economical viewpoint. Further, crazing or peeling sometimes takes place during drying of the coated layer.

In the present invention, the pore volume of the ink-receptive layer formed on the substrate sheet is measured by the following mercury penetration method.

About 0.2 to 0.3 g of a recording sheet with an ink-receptive layer prepared is placed in a measuring cell (volume: 0.5 cc), and a pore distribution is measured by the use of a QUANTA CHROME AUTOSCAN-60 POROSIMETER under the conditions of a mercury contact angle of 130°, a mercury surface tension of 473 $dyn/cm^2$ and a measuring range of "high pressure". From the pore distribution measured, a pore volume of pores of 3.4 to 30 nm and a pore volume of pores of 30 to 2000 nm are obtained, and from the weight of the receptive layer in the recording sheet, a pore volume based on 1 g of the receptive layer is determined.

Coating Liquid for Forming Ink-Receptive Layer

In the coating liquid for forming an ink-receptive layer according to the invention, (i) the fibrous crystalline particles on surfaces of which a cationic hydrated metal compound is supported and (ii) the binder are dispersed in a dispersion medium consisting of water and/or an organic solvent.

Examples of the components of the coating liquid include the same substances as previously described.

As the organic solvent, isopropyl alcohol, ethanol, butanol or the like can be used singly or in combination.

The concentration of the cationic hydrated metal compound-supported fibrous crystalline particles (i) in the coating liquid is properly determined according to the coating method used, and it is desired to be in the range of preferably 2 to 40% by weight, particularly preferably 5 to 30% by weight. The amount of the binder is in the range of preferably 5 to 60% by weight, more preferably 10 to 40% by weight, based on the cationic hydrated metal compound-supported fibrous crystalline particles.

For the purpose of enhancing adhesion of the ink-receptive layer to the substrate sheet or increasing strength and weathering resistance of the ink-receptive layer or controlling a pore structure of the ink-receptive layer, the coating liquid of the invention may contain antioxidants, organic polymers such as celluloses, bio-fibers, inorganic polymers, inorganic fine particles, etc., as previously described.

In the recording sheet with an ink-receptive layer according to the invention, the ink-receptive layer comprises (i) fibrous crystalline particles on surfaces of which a cationic hydrated metal compound is supported and (ii) a binder. Therefore, the pore volume of pores having a specific pore diameter range is large and the surface has a high streaming potential. On this account, the ink-receptive layer exhibits a high ink absorption rate, and dyes can be firmly fixed to the layer, so that the ink-receptive layer has excellent water resistance, weathering resistance and heat resistance. Further, because the cationic hydrated metal compound-supported fibrous crystalline particles are fibrous, the ink-receptive layer has high strength. Furthermore, the recording sheet with such an ink-receptive layer exhibits excellent printing properties and enables clear printing even if printing is carried out using various inks, irrespective of the printing method. Moreover, the recording sheet with such an ink-receptive layer is favorable also for printing using pigment type inks.

By the use of the coating liquid for forming an ink-receptive layer according to the invention, an ink-receptive layer having such excellent properties as described above can be formed.

EXAMPLES

The present invention is further described with reference to the following examples, but it should be construed that the invention is in no way limited to or by those examples.

Example 1

Preparation of Cationic Hydrated Metal Compound-Supported Fibrous Crystalline Particles (1) for Forming Ink-Receptive Layer In a 13.8 kg of pure water, 2 kg of basic magnesium sulfate (available from Ube Materials Industries, Ltd., Mos Hige, solids concentration: 84% by weight, average fiber diameter: 0.75 μm, average fiber length: 12 μm) as a basic alkaline earth metal sulfate compound was dispersed to prepare a slurry. To the slurry, 679.3 g of a cationic hydrated metal compound (available from Oki Kagaku K.K., PAC #1000, $Al_2O_3$: 23.34% by weight, Cl: 8.06% by weight, basicity: 83.44%) was added so that the molar ratio to the basic magnesium sulfate should become 0.36, followed by stirring at 25° C. for 60 minutes. Then, the solids were separated by filtration, dried at 110° C. for 16 hours and pulverized by a mixer (manufactured by Hitachi, Ltd., VA-W-27) to prepare a powder of cationic hydrated metal compound-supported fibrous crystalline particles (1) for forming an ink-receptive layer. In the pulverization using a mixer, the fibrous crystalline particles were hardly pulverized, and aggregates thereof were disaggregated.

The powder of the cationic hydrated metal compound-supported fibrous crystalline particles (1) had an average fiber diameter of 0.75 μm, an average fiber length of 12 μm and a streaming potential of 31 μeq/g.

Preparation of Coating Liquid (1) for Forming Ink-Receptive Layer

86 Parts by weight of a dispersion obtained by dispersing the above-obtained powder of the cationic hydrated metal compound-supported fibrous crystalline particles (1) in water so that the solids concentration should become 11.4% by weight and 14 parts by weight of a polyvinyl alcohol aqueous solution having a concentration of 10% by weight were mixed to prepare a coating liquid (1) for forming an ink-receptive layer.

Preparation of Recording Sheet (1)

Subsequently, the coating liquid (1) was applied onto a PET film by the use of a bar coater, dried and then subjected to heat treatment at 140° C. to prepare a recording sheet (1). The ink-receptive layer had a thickness of 30 μm. The pore volume of the ink-receptive layer was measured by the aforesaid mercury penetration method.

Then, printing was carried out on the resulting recording sheet (1) in the following manner, and the print was evaluated.

The results are set forth in Table 1.

Printing

On the resulting recording sheet, a solid pattern W of 2 cm square was printed by an ink jet printer (manufactured by GRAPHTEC Co., Masterjet) using genuine dye inks and pigment inks. Colors of magenta, black, cyan and yellow were used, and for each printing, an output power was altered to change density.

Density

The density was measured by a color reflection densitometer (manufactured by Nippon Denshoku Industries Co., Ltd., KRD-2200). When the density is not less than 1.2, the print is employable without any problem.

Blotting

The shape of each printed dot was observed by a microscope, and evaluation was carried out according to the following criteria.

AA: The dot is completely circular, and no blot is observed.
BB: The dot is circular, but a slight blot is observed.
CC: The dot is circular, but a marked blot is observed.

Drying Rate

Different two-color dots overlapping each other were observed by a microscope to examine mixing of colors, and evaluation was carried out according to the following criteria.

AA: Mixing of colors is not observed.
BB: Mixing of colors is slightly observed.
CC: Mixing of colors is markedly observed.

Water Resistance

A strip of the resulting print was immersed in water to observe elution of dye or pigment, and evaluation was carried out according to the following criteria.

AA: No blot is observed.
BB: A blot is slightly observed.
CC: A blot is markedly observed.
DD: Elution of dye or pigment is observed.

Crocking

A printed part of the print using pigment ink was rubbed with a finger to examine change of image quality and adhesion of the pigment to the finger. Then, evaluation was carried out according to the following criteria.

AA: Change of image quality and adhesion of pigment are not observed.
BB: Change of image quality or adhesion of pigment is observed.

Example 2

Preparation of Cationic Hydrated Metal Compound-Supported Fibrous Crystalline Particles (2) for Forming Ink-Receptive Layer A powder of cationic hydrated metal compound-supported fibrous crystalline particles (2) for forming an ink-receptive layer was prepared in the same manner as in Example 1, except that 905.7 g of a cationic hydrated metal compound (available from Oki Kagaku K.K., PAC #1000, $Al_2O_3$: 23.34% by weight, Cl: 8.06% by weight, basicity: 83.44%) was added so that the molar ratio to the basic magnesium sulfate should become 0.48. The powder of the cationic hydrated metal compound-supported fibrous crystalline particles (2) had an average fiber diameter of 0.75 μm, an average fiber length of 12 μm and a streaming potential of 42 μeq/g.

Preparation of Coating Liquid (2) for Forming Ink-Receptive Layer

A coating liquid (2) for forming an ink-receptive layer was prepared in the same manner as in Example 1, except that the powder of the cationic hydrated metal compound-supported fibrous crystalline particles (2) was used.

Preparation of Recording Sheet (2)

Subsequently, the coating liquid was applied onto a PET film by the use of a bar coater, dried and then subjected to heat treatment at 140° C. to prepare a recording sheet (2). The ink-receptive layer had a thickness of 30 μm. Then, printing was carried out on the resulting recording sheet in the same manner as in Example 1, and the print was evaluated.

The results are set forth in Table 1.

Example 3

Preparation of Coating Liquid (3) for Forming Ink-Receptive Layer

A coating liquid (3) for forming an ink-receptive layer was prepared in the same manner as in Example 1, except that 91 parts by weight of a dispersion obtained by dispersing the powder of the cationic hydrated metal compound-supported fibrous crystalline particles (1) in water so that the solids concentration should become 11.4% by weight and 9 parts by weight of a polyvinyl alcohol aqueous solution having a concentration of 10% by weight were mixed.

Preparation of Recording Sheet (3)

Subsequently, the coating liquid was applied onto a PET film by the use of a bar coater, dried and then subjected to heat treatment at 140° C. to prepare a recording sheet (3). The ink-receptive layer had a thickness of 30 μm. Then, printing was carried out on the resulting recording sheet in the same manner as in Example 1, and the print was evaluated.

The results are set forth in Table 1.

Example 4

Preparation of Coating Liquid (4) for Forming Ink-Receptive Layer

A coating liquid (4) for forming an ink-receptive layer was prepared in the same manner as in Example 1, except that 80 parts by weight of a dispersion obtained by dispersing the powder of the cationic hydrated metal compound-supported fibrous crystalline particles (1) in water so that the solids concentration should become 11.4% by weight and 20 parts by weight of a polyvinyl alcohol aqueous solution having a concentration of 10% by weight were mixed.

Preparation of Recording Sheet (4)

Subsequently, the coating liquid was applied onto a PET film by the use of a bar coater, dried and then subjected to heat treatment at 140° C. to prepare a recording sheet (4). The ink-receptive layer had a thickness of 30 μm. Then, printing was carried out on the resulting recording sheet in the same manner as in Example 1, and the print was evaluated.

The results are set forth in Table 1.

Example 5

Preparation of Cationic Hydrated Metal Compound-Supported Fibrous Crystalline Particles (5) for Forming Ink-Receptive Layer In a 13.8 kg of pure water, 2 kg of basic magnesium sulfate (available from Ube Materials Industries, Ltd., Mos Hige, solids concentration: 84% by weight, average fiber diameter: 0.75 μm, average fiber length: 12 μm) as a basic alkaline earth metal sulfate compound was dispersed to prepare a slurry. To the slurry, 468.1 g of a zirconium oxychloride aqueous solution (available from Kanto Kagaku K.K., $ZrO_3$ concentration: 10% by weight) as a cationic hydrated metal compound was added so that the molar ratio to the basic magnesium sulfate should become 0.36, followed by stirring at 25° C. for 60 minutes. Then, the solids were separated by filtration, dried at 110° C. for 16 hours and pulverized by a mixer (manufactured by Hitachi, Ltd., VA-W-27) to prepare a powder of cationic hydrated metal compound-supported fibrous crystalline particles (5) for forming an ink-receptive layer. The powder of the cationic hydrated metal compound-supported fibrous crystalline particles (5) had an average fiber diameter of 0.75 μm, an average fiber length of 12 μm and a streaming potential of 18 μeq/g.

Preparation of Coating Liquid (5) for Forming Ink-Receptive Layer

86 Parts by weight of a dispersion obtained by dispersing the above-obtained powder of the cationic hydrated metal compound-supported fibrous crystalline particles (5) in water so that the solids concentration should become 11.4% by weight and 14 parts by weight of a polyvinyl alcohol aqueous solution having a concentration of 10% by weight were mixed to prepare a coating liquid (5) for forming an ink-receptive layer.

Preparation of Recording Sheet (5)

Subsequently, the coating liquid (5) was applied onto a PET film by the use of a bar coater, dried and then subjected to heat treatment at 140° C. to prepare a recording sheet (5). The ink-receptive layer had a thickness of 30 μm. The pore volume of the ink-receptive layer was measured by the aforesaid mercury penetration method.

Then, printing was carried out on the resulting recording sheet (5) in the same manner as in Example 1, and the print was evaluated.

The results are set forth in Table 1.

Example 6

Preparation of Cationic Hydrated Metal Compound-Supported Fibrous Crystalline Particles (6) for Forming Ink-receptive Layer A powder of cationic hydrated metal compound-supported fibrous crystalline particles (6) was prepared in the same manner as in Example 1, except that 2 kg of calcium silicate (available from Ube Materials Industries Ltd., Zono Hige, solids concentration: 97% by weight, average fiber diameter: 0.3 μm, average fiber length: 6 μm) was used as fibrous crystalline particles. The powder of the cationic hydrated metal compound-supported fibrous crystalline particles (6) had an average fiber diameter of 0.3 μm, an average fiber length of 3 μm and a streaming potential of 12 μeq/g.

Preparation of Coating Liquid (6) for Forming Ink-Receptive Layer

86 Parts by weight of a dispersion obtained by dispersing the above-obtained powder of the cationic hydrated metal compound-supported fibrous crystalline particles (6) in water so that the solids concentration should become 11.4% by weight and 14 parts by weight of a polyvinyl alcohol aqueous solution having a concentration of 10% by weight were mixed to prepare a coating liquid (6) shown in Table 1.

Preparation of Recording Sheet (6)

Subsequently, the coating liquid (6) was applied onto a PET film by the use of a bar coater, dried and then subjected to heat treatment at 140° C. to prepare a recording sheet (6). The ink-receptive layer had a thickness of 30 μm. The pore volume of the ink-receptive layer was measured by the aforesaid mercury penetration method.

Then, printing was carried out on the resulting recording sheet (6) in the same manner as in Example 1, and the print was evaluated.

The results are set forth in Table 1.

Example 7

Preparation of Coating Liquid (7) for Forming Ink-Receptive Layer

A coating liquid (7) for forming an ink-receptive layer was prepared in the same manner as in Example 6, except that 80 parts by weight of a dispersion obtained by dispersing the powder of the cationic hydrated metal compound-supported fibrous crystalline particles (6) in water so that the solids concentration should become 11.4% by weight and 20 parts by weight of a polyvinyl alcohol aqueous solution having a concentration of 10% by weight were mixed.

Preparation of Recording Sheet (7)

Subsequently, the coating liquid (7) was applied onto a PET film by the use of a bar coater, dried and then subjected to heat treatment at 140° C. to prepare a recording sheet (7). The ink-receptive layer had a thickness of 30 μm. The pore volume of the ink-receptive layer was measured by the aforesaid mercury penetration method.

Then, printing was carried out on the resulting recording sheet (7) in the same manner as in Example 1, and the print was evaluated.

The results are set forth in Table 1.

Example 8

Preparation of Coating Liquid (8) for Forming Ink-Receptive Layer

61 Parts by weight of a dispersion obtained by dispersing the particles (1) for forming an ink-receptive layer, said powder being obtained in the same manner as in Example 1, in water so that the solids concentration should become 11.4% by weight, 25 parts by weight of a sol obtained by diluting an alumina sol (available from Catalysts & Chemicals Industries Co., Ltd., Cataloid AS-3, average particle diameter: 200 nm, primary particle diameter: 9 nm, pseudo-boehmite alumina) with water so that the solids concentration should become 11.4% by weight and 14 parts by weight of a polyvinyl alcohol aqueous solution having a concentration of 10% by weight were mixed to prepare a coating liquid (8) for forming an ink-receptive layer.

Preparation of Recording Sheet (8)

Subsequently, the coating liquid was applied onto a PET film by the use of a bar coater, dried and then subjected to heat treatment at 140° C. to prepare a recording sheet (8). The ink-receptive layer had a thickness of 30 μm. Then, printing was carried out on the resulting recording sheet in the same manner as in Example 1, and the print was evaluated.

The results are set forth in Table 1.

Example 9

Preparation of Coating Liquid (9) for Forming Ink-Receptive Layer

57 Parts by weight of a dispersion obtained by dispersing the particles (1) for forming an ink-receptive layer, said powder being obtained in the same manner as in Example 1, in water so that the solids concentration should become 11.4% by weight, 29 parts by weight of a dispersion obtained by diluting a silica sol (available from Catalysts & Chemicals Industries Co., Ltd., Cataloid SI-50, average particle diameter: 25 nm) with water so that the solids concentration should become 11.4% by weight and 14 parts by weight of a polyvinyl alcohol aqueous solution having a concentration of 10% by weight were mixed to prepare a coating liquid (9) for forming an ink-receptive layer.

Preparation of Recording Sheet (9)

Subsequently, the coating liquid was applied onto a PET film by the use of a bar coater, dried and then subjected to heat treatment at 140° C. to prepare a recording sheet (9). The ink-receptive layer had a thickness of 30 μm. Then, printing was carried out on the resulting recording sheet in the same manner as in Example 1, and the print was evaluated.

The results are set forth in Table 1.

Comparative Example 1

Preparation of Coating Liquid (R1) for Forming Ink-Receptive Layer

86 Parts by weight of a dispersion obtained by dispersing basic magnesium sulfate (available from Ube Materials Industries Ltd., Mos Hige, solids concentration: 84% by weight, average fiber diameter: 0.75 μm, average fiber length: 12 μm) in water so that the solids concentration should become 11.4% by weight and 14 parts by weight of a polyvinyl alcohol aqueous solution having a concentration of 11.4% by weight were mixed to prepare a coating liquid (R1).

Preparation of Recording Sheet (R1)

Subsequently, the coating liquid was applied onto a PET film by the use of a bar coater, dried and then subjected to heat treatment at 140° C. to prepare a recording sheet (R1). The ink-receptive layer had a thickness of 30 μm. The pore volume of the ink-receptive layer was measured by the aforesaid mercury penetration method.

Then, printing was carried out on the resulting recording sheet (R1) in the same manner as in Example 1, and the print was evaluated.

The results are set forth in Table 1.

Comparative Example 2

Preparation of Coating Liquid (R2) for Forming Ink-Receptive Layer

86 Parts by weight of a dispersion obtained by dispersing calcium silicate (available from Ube Materials Industries Ltd., Zono Hige, solids concentration: 97% by weight, average fiber diameter: 0.3 μm, average fiber length: 3 μm) in water so that the solids concentration should become 11.5% by weight and 14 parts by weight of a polyvinyl alcohol aqueous solution having a concentration of 10% by weight were mixed to prepare a coating liquid (R2).

Preparation of Recording Sheet (R2)

Subsequently, the coating liquid was applied onto a PET film by the use of a bar coater, dried and then subjected to heat treatment at 140° C. to prepare a recording sheet (R2). The ink-receptive layer had a thickness of 30 μm. The pore volume of the ink-receptive layer was measured by the aforesaid mercury penetration method.

Then, printing was carried out on the resulting recording sheet (R2) in the same manner as in Example 1, and the print was evaluated.

The results are set forth in Table 1.

Comparative Example 3

Preparation of Coating Liquid (R3) for Forming Ink-Receptive Layer

86 Parts by weight of a dispersion obtained by dispersing an alumina sol (available from Catalysts & Chemicals Industries Co., Ltd., Cataloid AS-3, average particle diameter: 200 nm, primary particle diameter: 9 nm, pseudo-boehmite alumina) in water so that the solids concentration should become 11.4% by weight and 14 parts by weight of a polyvinyl alcohol aqueous solution having a concentration of 10% by weight were mixed to prepare a coating liquid (R3).

Preparation of Recording Sheet (R3)

Subsequently, the coating liquid was applied onto a PET film by the use of a bar coater, dried and then subjected to heat treatment at 140° C. to prepare a recording sheet (R3). The ink-receptive layer had a thickness of 30 μm. Then, printing was carried out on the resulting recording sheet in the same manner as in Example 1, and the print was evaluated.

The results are set forth in Table 1.

TABLE 1

| | Reaction product for forming ink-receptive layer | | | | | | Ink-receptive layer | | | |
| --- | --- | --- | --- | --- | --- | --- | --- | --- | --- | --- |
| | Fibrous crystalline particles | | | | Supported cation | Streaming potential $\mu eq/g$ | Film thickness $\mu m$ | Fibrous crystalline particles wt % | Inorganic fine particles wt % | Binder wt % | Pore volume 30-2000 nm ml/g |
| | Type | Average fiber diameter $\mu m$ | Average fiber length $\mu m$ | Aspect ratio | Type | Amount (wt % in terms of oxide) | | | | | | |
| Ex. 1 | A | 0.75 | 12 | 16 | Al | 10 | 31 | 30 | 88 | | 12 | 0.25 |
| Ex. 2 | A | 0.75 | 12 | 16 | Al | 13 | 42 | 30 | 88 | | 12 | 0.35 |
| Ex. 3 | A | 0.75 | 12 | 16 | Al | 10 | 31 | 30 | 92 | | 8 | 0.25 |
| Ex. 4 | A | 0.75 | 12 | 16 | Al | 10 | 31 | 30 | 82 | | 18 | 0.25 |
| Ex. 5 | A | 0.75 | 12 | 16 | Zr | 3 | 18 | 30 | 88 | | 12 | 0.25 |
| Ex. 6 | B | 0.3 | 3 | 10 | Al | 8 | 12 | 30 | 88 | | 12 | 0.20 |
| Ex. 7 | B | 0.3 | 3 | 10 | Al | 8 | 12 | 30 | 82 | | 18 | 0.20 |
| Ex. 8 | A | 0.75 | 12 | 16 | Al | 10 | 50 | 30 | 88 | 25 | 12 | 0.20 |
| Ex. 9 | A | 0.75 | 12 | 16 | Al | 10 | 30 | 30 | 63 | 30 | 12 | 0.20 |
| Comp. Ex. 1 | A | 0.75 | 12 | 16 | Not reacted | | −5 | 30 | 88 1) | | 12 | 0.50 |
| Comp. Ex. 2 | B | 0.3 | 3 | 10 | Not reacted | | −5 | 30 | 88 1) | | 12 | 0.20 |
| Comp. Ex. 3 | $Al_2O_3$ | 0.04 | 0.2 | 5 | Not reacted | | 10 | 30 | | 88 | 12 | 0.15 |

| | Evaluation of print | | | | | | | |
| --- | --- | --- | --- | --- | --- | --- | --- | --- |
| | Dye ink | | | | Pigment ink | | | |
| | Water resistance | Density | Blotting | Drying rate | Density | Blotting | Drying rate | Crocking |
| Ex. 1 | AA | 1.7 | AA | AA | 1.6 | AA | AA | AA |
| Ex. 2 | AA | 1.8 | AA | AA | 1.7 | AA | AA | AA |
| Ex. 3 | AA | 1.7 | AA | AA | 1.6 | AA | AA | AA |
| Ex. 4 | AA | 1.7 | AA | AA | 1.6 | AA | AA | AA |
| Ex. 5 | AA | 1.6 | AA | AA | 1.5 | AA | AA | AA |
| Ex. 6 | BB | 1.5 | AA | AA | 1.5 | AA | AA | AA |
| Ex. 7 | BB | 1.5 | AA | AA | 1.5 | AA | AA | AA |
| Ex. 8 | AA | 1.7 | AA | BB | 1.6 | BB | BB | AA |
| Ex. 9 | BB | 1.5 | AA | BB | 1.5 | BB | BB | AA |

TABLE 1-continued

| | | | | | | | | |
|---|---|---|---|---|---|---|---|---|
| Comp. Ex. 1 | CC | 1.1 | CC | AA | 1.5 | AA | AA | AA |
| Comp. Ex. 2 | CC | 1.1 | CC | AA | 1.2 | AA | AA | AA |
| Comp. Ex. 3 | BB | 1.4 | CC | CC | 1.0 | CC | CC | BB |

A: basic magnesium sulfate
B: calcium silicate
1): In comparative Examples 1 to 2, each value means a weight of not a reaction product but particles.

The invention claimed is:

1. A recording sheet with an ink-receptive layer, comprising a substrate sheet and an ink-receptive layer formed thereon, wherein the ink-receptive layer comprises:
(i) fibrous crystalline particles on surfaces of which a cationic hydrated metal compound is supported, wherein the fibrous crystalline particles have an average fiber diameter (D) of 0.1 to 2 μm, an average fiber length (L) of 1 to 200 μm, and a ratio (aspect ratio) of an average fiber length (L) to an average fiber diameter (D) of 5 to 500, and
(ii) a binder,
wherein the fibrous crystalline particles are particles of at least one substance selected from the group consisting of basic magnesium sulfate, basic calcium sulfate, basic barium sulfate, and basic strontium sulfate.

2. The recording sheet with an ink-receptive layer as claimed in claim 1, wherein the cationic hydrated metal compound is a compound represented by the following formula (1) or a compound obtained from a metal salt represented by the following formula (2):

$$[M_2(OH)_n X_{(2a-n)/b}]_m \quad (1)$$

$$[MX_{a/b}]_m \quad (2)$$

wherein M is a trivalent or higher metallic cation, X is an anion, a is a valence of the metallic cation, b is a valence of the anion, and n and m are numbers satisfying the conditions of $1<n<5$, $n<2a$ and $1\leq m$.

3. The recording sheet with an ink-receptive layer as claimed in claim 2, wherein M of the cationic hydrated metal compound is $Al^{3+}$.

4. The recording sheet with an ink-receptive layer as claimed in claim 1, which further comprises inorganic fine particles.

5. The recording sheet with an ink-receptive layer as claimed in claim 4, wherein the inorganic fine particles are one or more substances selected from an alumina sol, an alumina gel, a silica sol, a silica gel, a silica-alumina sol, a silica-alumina gel, a zirconia sol, a zirconia gel and a clay mineral.

6. The recording sheet with an ink-receptive layer as claimed in claim 5, wherein the inorganic fine particles are an alumina sol and/or an alumina gel each of which is pseudo-boehmite alumina.

7. The recording sheet with an ink-receptive layer as claimed in claim 1, wherein the ink-receptive layer has pores having pore diameters of 30 to 2000 nm, and a pore volume of the pores having pore diameters of 30 to 2000 nm is in the range of 0.15 to 2.0 ml/g.

8. The recording sheet with an ink-receptive layer as claimed in claim 2, which further comprises inorganic fine particles.

9. The recording sheet with an ink-receptive layer as claimed in claim 3, which further comprises inorganic fine particles.

10. The recording sheet with an ink-receptive layer as claimed in claim 2, wherein the ink-receptive layer has pores having pore diameters of 30 to 2000 nm, and a pore volume of the pores having pore diameters of 30 to 2000 nm is in the range of 0.15 to 2.0 ml/g.

11. The recording sheet with an ink-receptive layer as claimed in claim 4, wherein the ink-receptive layer has pores having pore diameters of 30 to 2000 nm, and a pore volume of the pores having pore diameters of 30 to 2000 nm is in the range of 0.15 to 2.0 ml/g.

12. The recording sheet with an ink-receptive layer as claimed in claim 1, wherein the fibrous crystalline particles are particles of basic magnesium sulfate.

* * * * *